United States Patent
Bennett

Patent Number: 6,013,083
Date of Patent: Jan. 11, 2000

[54] ARTHROSCOPIC ROTATOR CUFF REPAIR APPARATUS AND METHOD

[76] Inventor: William F. Bennett, 5741 Bee Ridge Rd., No. 470, Sarasota, Fla. 34233

[21] Appl. No.: 08/850,526

[22] Filed: May 2, 1997

[51] Int. Cl.⁷ .................................................. A61B 17/58
[52] U.S. Cl. ........................................ 606/104; 606/232
[58] Field of Search ........................... 606/74, 103, 104, 606/96, 97, 98, 86, 232

[56] References Cited

U.S. PATENT DOCUMENTS

| | | | |
|---|---|---|---|
| 5,047,034 | 9/1991 | Sohngen | 606/87 |
| 5,163,940 | 11/1992 | Bourque | 606/96 |
| 5,522,844 | 6/1996 | Johnson | 606/232 |
| 5,527,341 | 6/1996 | Gogolewski et al. | 606/232 |
| 5,662,650 | 9/1997 | Bailey et al. | 606/59 |
| 5,797,932 | 8/1998 | Min et al. | 606/151 |
| 5,814,051 | 9/1998 | Wenstrom, Jr. | 606/104 |
| 5,814,072 | 9/1998 | Bonutti | 606/232 |

*Primary Examiner*—Michael Buiz
*Assistant Examiner*—Tan-Uyen T. Ho
*Attorney, Agent, or Firm*—Kenneth A. Roddy

[57] ABSTRACT

Torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

15 Claims, 8 Drawing Sheets

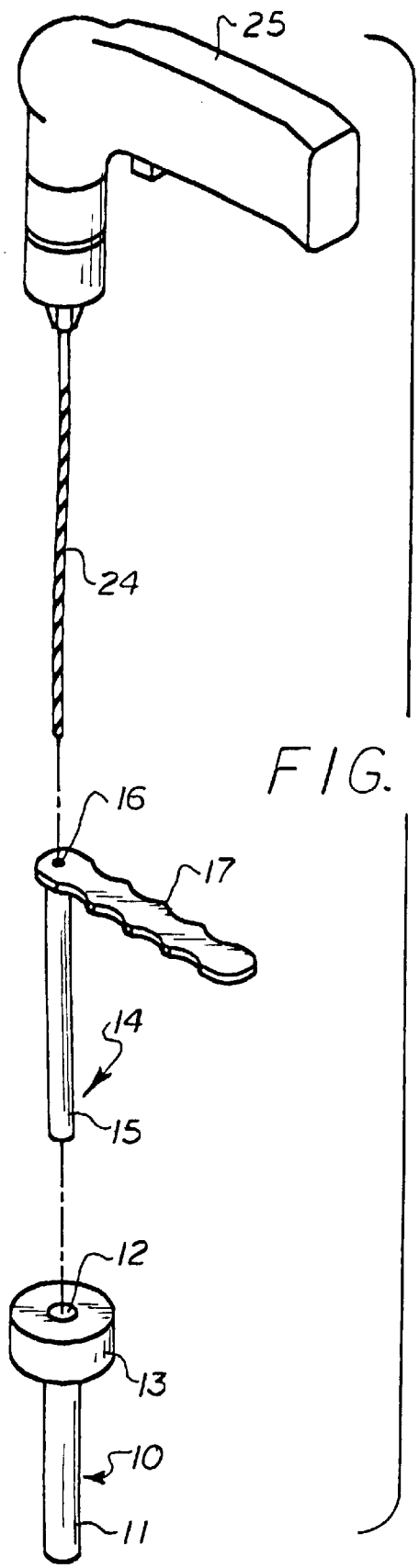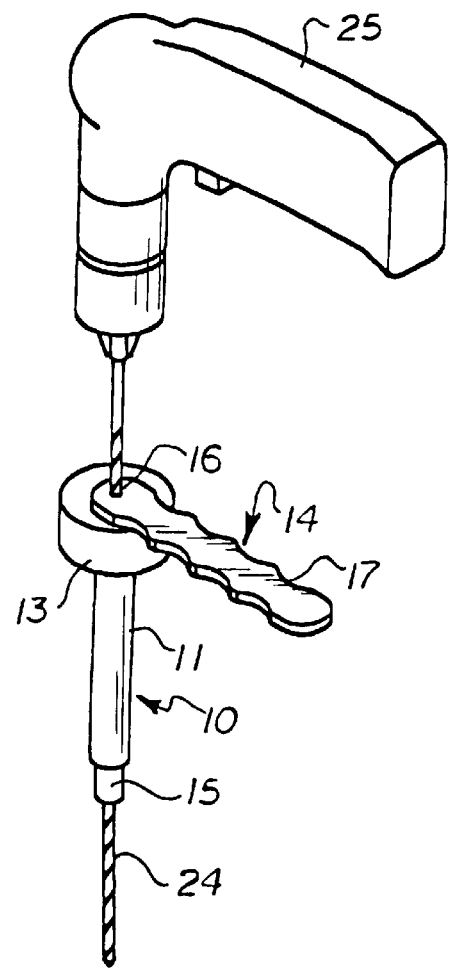
FIG. 1A
FIG. 1B

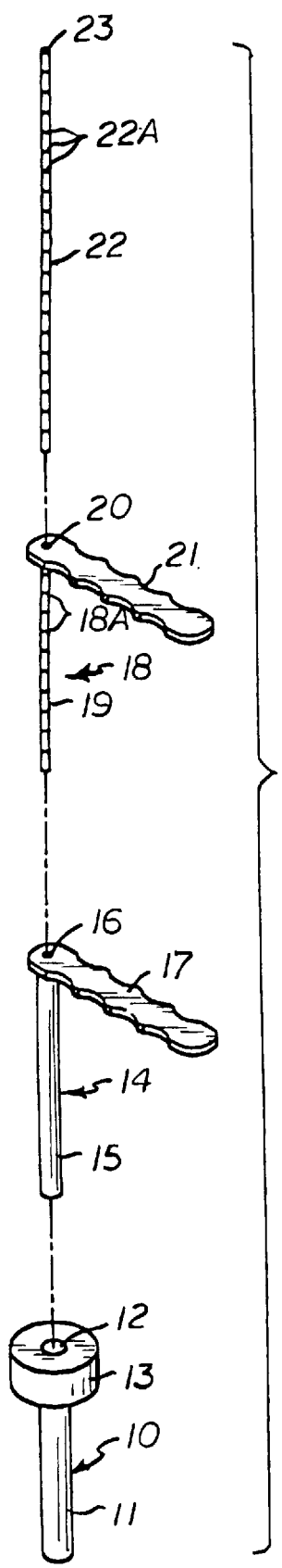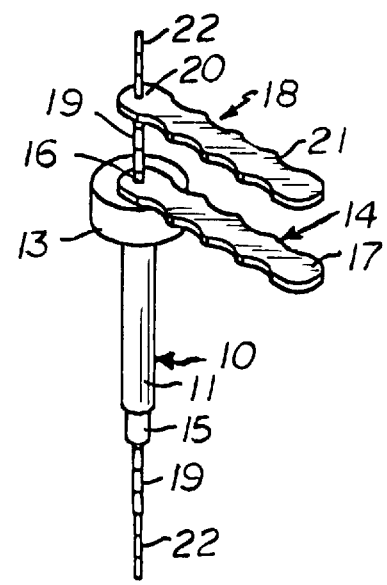
FIG. 2A
FIG. 2B

6,013,083

ARTHROSCOPIC ROTATOR CUFF REPAIR APPARATUS AND METHOD

BACKGROUND OF THE INVENTION

1. Field of the Invention

This invention relates generally to surgical apparatus and methods for repair of torn tissue, and more particularly to an apparatus and method for arthroscopic repair of a torn rotator cuff.

2. Brief Description of the Prior Art

The rotator cuff is composed of four tendons that blend together to help stabilize and move the shoulder. When a tear occurs in the rotator cuff of the shoulder, it is often necessary to re-attach the torn tendon or tendons to the bone of the humeral head.

In a common prior art rotator cuff reattachment technique, the torn cuff is punctured by a punch, and pre-threaded suture anchor screws (soft tissue fasteners) are drilled into the head of the humerus bone and the sutures threaded through the anchor screws are passed through the cuff in a difficult procedure using suture relay devices to pass the sutures through the tissue. After the suture strands are passed through the tissue, they are knotted and tied together to secure the reattached rotator cuff to the humerus head. Other types of prior art suture anchors are conically shaped members that are pressed into holes drilled into the bone and engage the cancellous mass surrounding the drilled hole.

A major problem with the above described suture anchoring technique is that the threaded suture anchor screws or conically shaped anchors are threadedly or otherwise secured to the cancellous bone mass beneath the near cortex of the head of the humerus, and depend on this cancellous mass for fixation. It is well known that the cancellous bone mass is susceptible to osteopenic changes (diminished amount of bone tissue).

As a result, the pull-out strength of suture anchors which are depend on the cancellous bone mass beneath the cortex of the bone is subject to becoming diminished with time, and the anchors will tend to loosen, thereby possibly requiring a second operation to remove the loosened suture anchor.

Another problem with the conventional technique is that, in most cases, the sutures are not passed through the tissue when the anchor is set, and thus a difficult procedural step is required using devices such as punches and suture relays to pass and tie the sutures through the torn tissue.

The present invention is distinguished over the prior art in general, by an apparatus and method for arthroscopic repair of torn tissue such as a rotator cuff wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

Unlike conventional soft tissues anchors which are anchored in the cancellous bone mass beneath the near cortex of the bone, the present invention provides a suture anchor which is engaged on the exterior of the far cortex of the bone and completely bypasses the cancellous bone mass. The cortex of the bone is much less susceptible to osteopenia than the cancellous interior of the bone.

With the present invention, the sutures are passed through the tissue when the anchor is set, and thus the difficult procedural step and use of devices such as punches and suture relays to pass and tie the sutures through the torn tissue is eliminated.

Calibrated markings on the deployment system of the present invention allow for precise measurement of the far cortex and precise measurement of the depth of insertion and engagement of the anchor device on the far cortex, such that structures beyond the cortex are not violated, and the button hold-down feature eliminates the traditionally difficult arthroscopic tying techniques.

SUMMARY OF THE INVENTION

It is therefore an object of the present invention to provide an apparatus and method for arthroscopic repair of torn tissue such as a rotator cuff which engages a suture anchor on the exterior of the far cortex of the bone and completely bypasses the cancellous bone mass.

It is therefore an object of the present invention to provide an apparatus and method for arthroscopic repair of torn tissue such as a rotator cuff which passes the sutures through the tissue when the anchor is set, and eliminates the difficult procedural step and use of devices such as punches and suture relays to pass and tie the sutures through the torn tissue.

Another object of this invention is to provide an apparatus and method for arthroscopic repair of torn tissue such as a rotator cuff which utilizes suture anchoring apparatus having calibrated markings for precise measurement of the far cortex and the depth of insertion and engagement of the anchor device on the far cortex, such that structures beyond the cortex are not violated.

A further object of this invention is to provide an apparatus and method for arthroscopic repair of torn tissue such as a rotator cuff that utilizes a button hold-down feature which substantially eliminates traditionally difficult arthroscopic suture tying techniques.

A still further object of this invention is to provide a an apparatus for arthroscopic repair of torn tissue such as a rotator cuff which is simple in construction, inexpensive to manufacture, and rugged and reliable in operation.

Other objects of the invention will become apparent from time to time throughout the specification and claims as hereinafter related.

The above noted objects and other objects of the invention are accomplished by the present invention wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

BRIEF DESCRIPTION OF THE DRAWINGS

FIG. 1A is an exploded perspective view of the cannula and drill guide components of the apparatus in accordance with the present invention.

FIG. 1B is a perspective view of the cannula and drill guide components shown in an assembled condition.

FIG. 2A is an exploded perspective view of the cannula, drill guide, inner cannula, and anchor deployment tool components of the apparatus.

FIG. 2B is a perspective view of the cannula, drill guide, inner cannula, and anchor deployment tool components shown in an assembled condition.

DESCRIPTION OF THE PREFERRED EMBODIMENT

Figure 3:
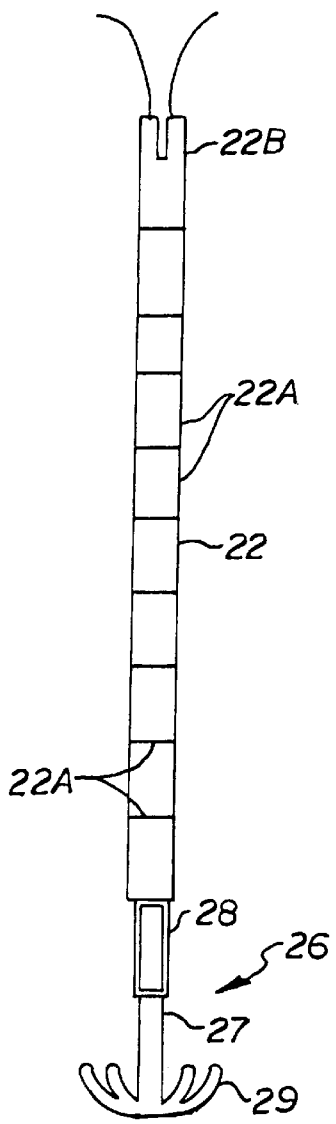
FIG. 3 is a side elevation of the suture anchor and anchor deployment tool in a releasably connected position.

Referring now to FIGS. 1A, 1B, 2A, and 2B of the drawings, the suture anchor installation apparatus in accordance with the present invention is shown schematically. The installation apparatus includes a conventional hollow cannula 10, having a tubular portion 11 with an axial bore 12 and a radial flange 13 at its proximal end; a hollow cannulated drill guide 14 having a tubular portion 15 with an axial bore 16 and a laterally extending handle 17 at its proximal end; a hollow inner cannula 18 having a tubular portion 19 with an axial bore 20 and a laterally extending handle 21 at its proximal end; and a tubular anchor deployment tool 22 having an axial bore 23.

The exterior surface of the tubular portion 19 of the inner cannula 18 and the exterior surface of the tubular anchor deployment tool 22 are provided with longitudinally spaced markings 19A and 22A, respectively, along their length in equal graduations. The tubular portion 15 of the drill guide 14 is sized to be slidably received through the axial bore 12 of the conventional cannula 10 with its distal end extending a distance outwardly from the distal end of the cannula 10 (FIG. 1B). The axial bore 16 of the drill guide 14 is sized to receive the bone drill bit 24 of a conventional air drill 25. The bone drill bit 24 may optionally be provided with longitudinally spaced markings (not shown) along its length in equal graduations corresponding to the markings 19A and 22A on the tubular portion 19 of the inner cannula 18 and the exterior surface of the tubular anchor deployment tool 22.

As best seen in FIGS. 2A and 2B, tubular portion 19 of the inner cannula 18 is sized to be slidably received through the axial bore 16 of the drill guide 14 and is of sufficient length such that its proximal and distal ends extend outwardly from the proximal and distal ends of the drill guide. The inner cannula 18 may also be provided in sizes to be received in the axial bore 12 of the conventional cannula 10 for use in situtations where the drill guide 14 is removed from the cannula 10. The tubular anchor deployment tool 22 is sized to be slidably received through the axial bore 20 of the inner cannula 18 and is of sufficient length such that its proximal and distal ends extend outwardly from the proximal and distal ends of the inner cannula (FIG. 2B). The sidewall of the deployment tool may be provided with a short longitudinal slot 22B at its proximal end through which the upper free ends of sutures may be received.

Figure 4:
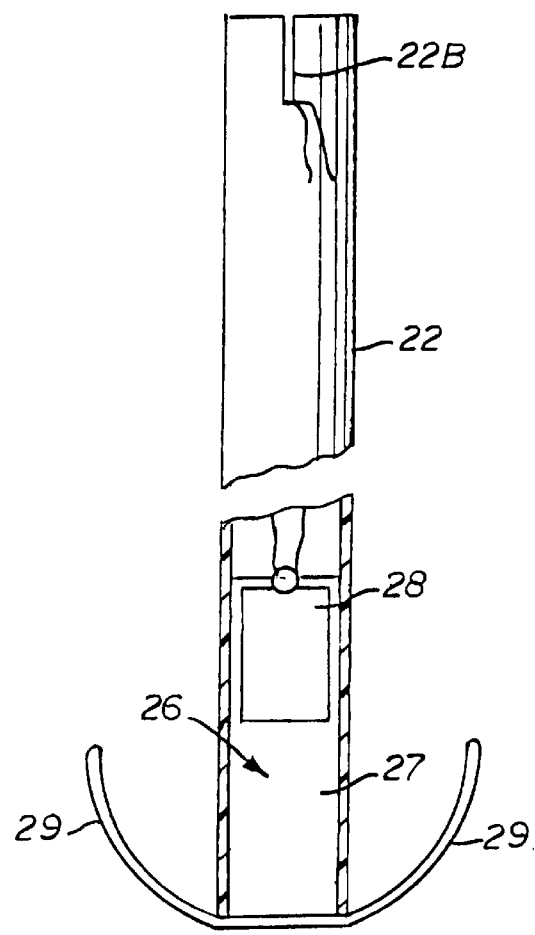
FIG. 4 is a side elevation showing the connection between the suture anchor and distal end of the anchor deployment tool.

Referring now to FIGS. 3 and 4 of the drawings, the soft tissue fastener or suture anchor 26 is shown somewhat schematically. The suture anchor 26 has a tubular shank 27 of predetermined length with an eyelet 28 at its proximal end and a plurality of circumferentially spaced wings 29 at its distal end which extend radially outward and rearwardly toward the proximal end of the anchor in the fashion of an inverted umbrella or grappling hook. The wings are resilient, such that they will be compressed and deflected radially inward when passed through a hole smaller in diameter than the wings in their outwardly extended state. The wings 29 are also of a predetermined length. In other words, if the total length of the anchor 26 is 1.5 cm., the longitudinal distance (height) of the wings 29 may be 0.5 cm.

Figure 5B:
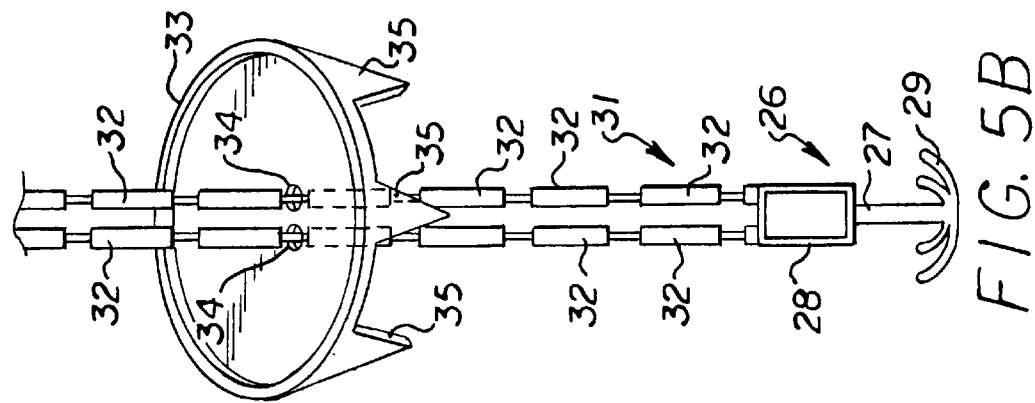
FIG. 5B is a perspective view showing the suture button with plastic strands having protuberances.
Figure 5A:
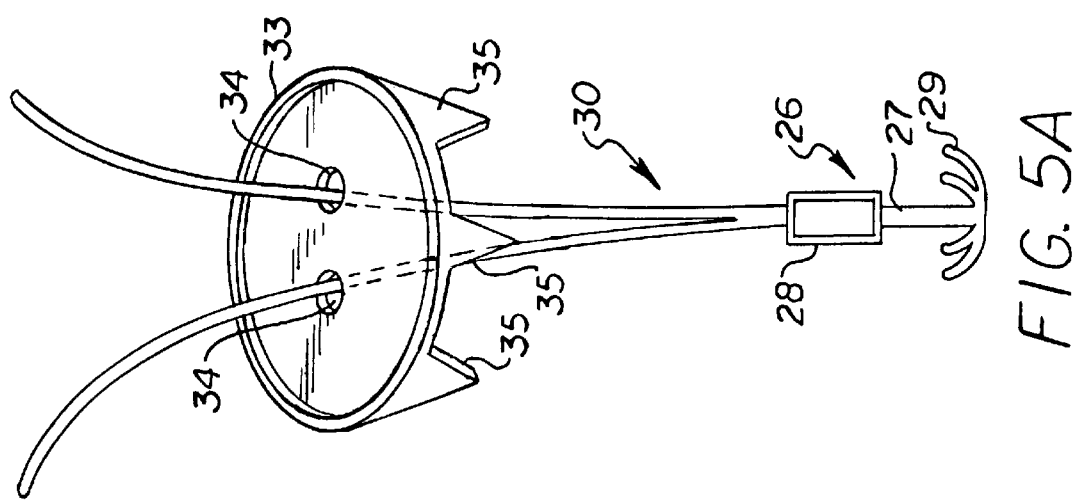
FIG. 5A is a perspective view showing the suture button with a conventional suture.

As shown in FIG. 5A, a conventional suture 30 may be secured to the eyelet 28 of the anchor 26 with two strands of the suture extending therefrom. Alternatively, as shown in FIG. 5B, a pair of special suture strands 31 may be secured to the eyelet 28. Each of the special suture strands 31 has a plurality of longitudinally spaced enlarged diameter portions or protuberances 32 along its length, similar to a plastic cable tie. The sutures 30 and 31 may be made of absorbable materials that absorb over a period of time, or they may be made of various non-absorbable, biocompatible materials.

A button 33 may be utilized with the anchor 26 and sutures 30 or 31 to attach the tendons of the rotator cuff to the bone. The button 33 is a disc-shaped member having two or more holes 34 through its flat surface through which the sutures 30 or 31 will pass. The protuberances 32 are slightly larger than the diameter of the holes 34 so as to snap through the holes upon sufficient force being applied. The button 33 may also have a plurality of circumferentially spaced prongs 35 depending from one side which can be pressed into the soft tissue of the rotator cuff.

INSTALLATION

Figure 6A:
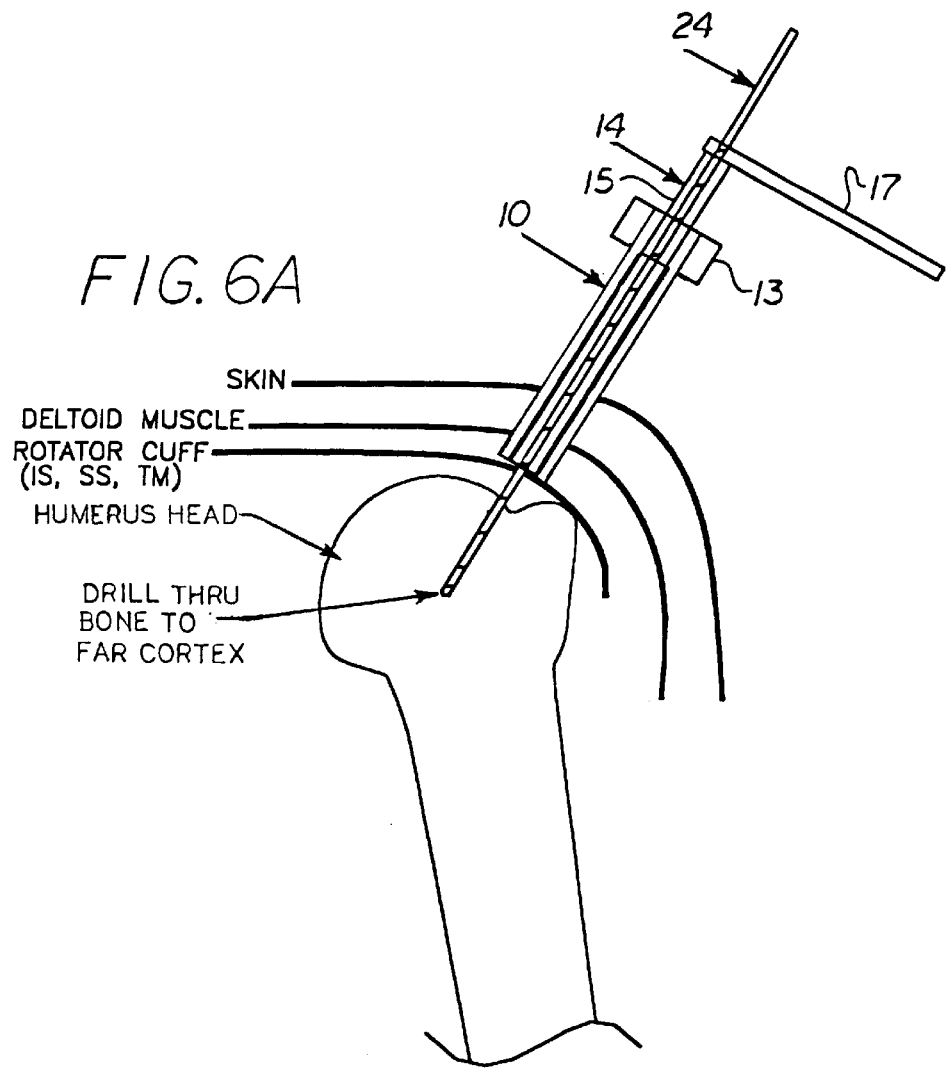
FIGS. 6A through 6E are schematic illustrations showing the various stages in installing the suture anchor.
Figure 6B:
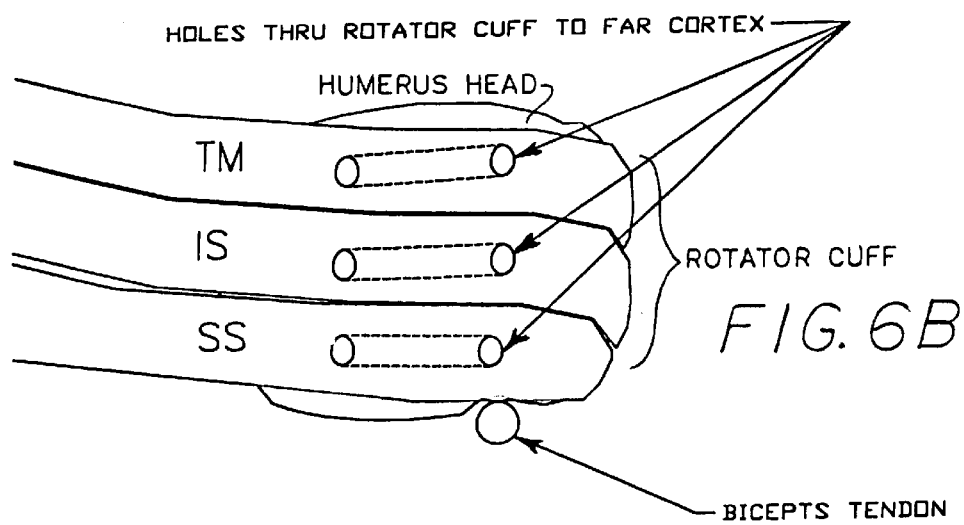

Referring now to FIGS. 6A through 6E, to install the soft tissue fastener or anchor 26, the rotator cuff is held in the proper position by a conventional tissue grasper through an auxiliary portal. The conventional cannula 10 is inserted through the skin and the deltoid muscle onto the rotator cuff. The tubular portion 15 of the drill guide 14 is installed through the axial bore 12 of the cannula 10 with its distal end engaged on the rotator cuff. The bone drill bit 24 of the air drill 25 is inserted through the axial bore 16 of the drill guide 14 (FIG. 2B). A hole is then drilled through the tendon of the rotator cuff and completely through the humerus head (FIG. 6A). The drill bit is removed and the depth of the hole is determined using a depth gage. FIG. 6B is a top plan view showing three tendons of the rotator cuff having holes drilled through the tendon and humerus head.

Figure 6C:
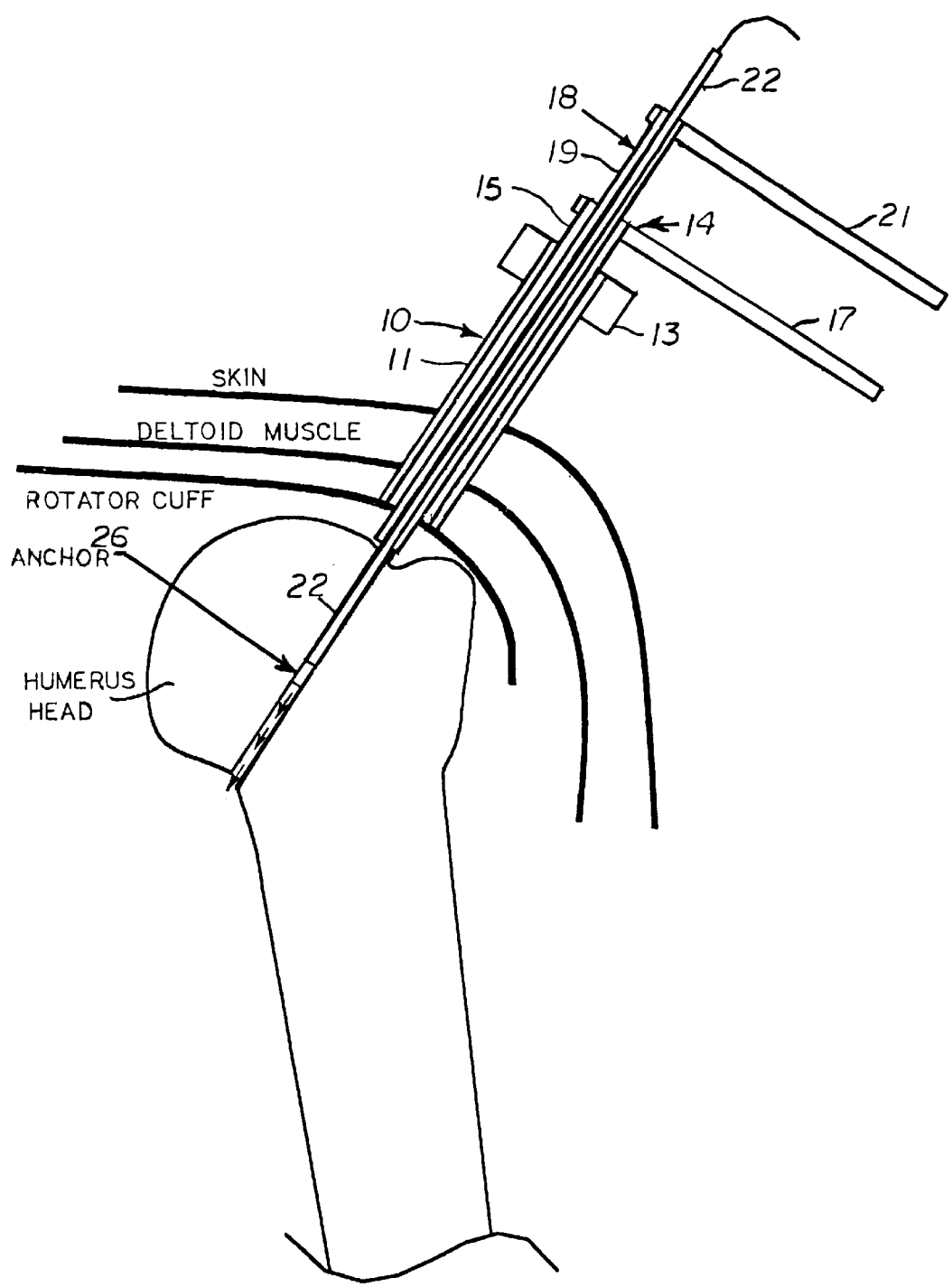
Figure 6D:
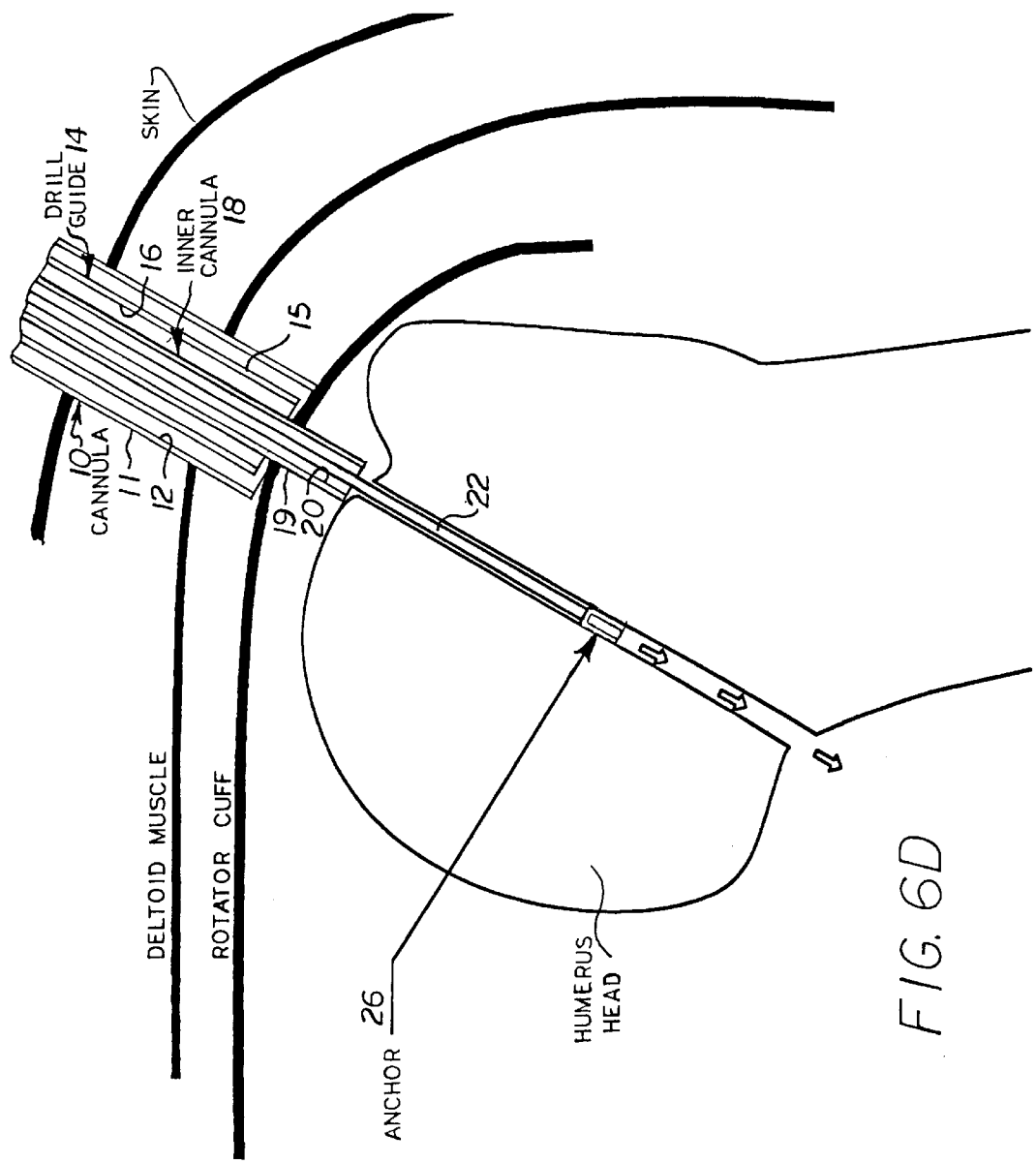

As shown in FIGS. 2B, 6C and 6D, the tubular portion 19 of the inner cannula 18 is installed through the axial bore 16 of the drill guide 14 and through the rotator cuff tendon with its distal end positioned adjacent to the distal end of the drill guide. Its position can be determined by the graduated markings on the exterior of its proximal end.

Alternatively, the tubular portion 19 of the inner cannula 18 may be installed through the axial bore of the drill guide 14, through the rotator cuff tendon, and through the drilled hole with its distal end positioned at the far cortex of the humerus head (bottom of the hole). Its position can be determined by the graduated markings on the exterior of its proximal end. In some cases, the drill guide 14 may be removed from the conventional cannula 10 and the tubular portion 19 of the inner cannula 18 installed in the axial bore 12 of the conventional cannula 10.

The soft tissue fastener or anchor 26 is releasably connected to the distal end of the deployment tool 22. In one preferred connection embodiment, the tubular shank 27 and eyelet 28 of the anchor is slidably received inside the distal end of the deployment tool 22 with the strands of the suture 30 or 31 extending upwardly through the interior of the deployment tool 22. The upper free ends of the sutures 30 or 31 are pulled upwardly and placed through a slot 22B in the sidewall of the deployment tool 22 to releasably retain the anchor 26 at the distal end to the deployment tool.

The assembled deployment tool 22 and anchor 26 is then inserted through the axial bore 20 of the inner cannula 18, causing the outwardly extended wings 29 of the anchor to become compressed and deflected radially inward by the interior of the inner cannula 18 as they pass therethrough.

Figure 6E:
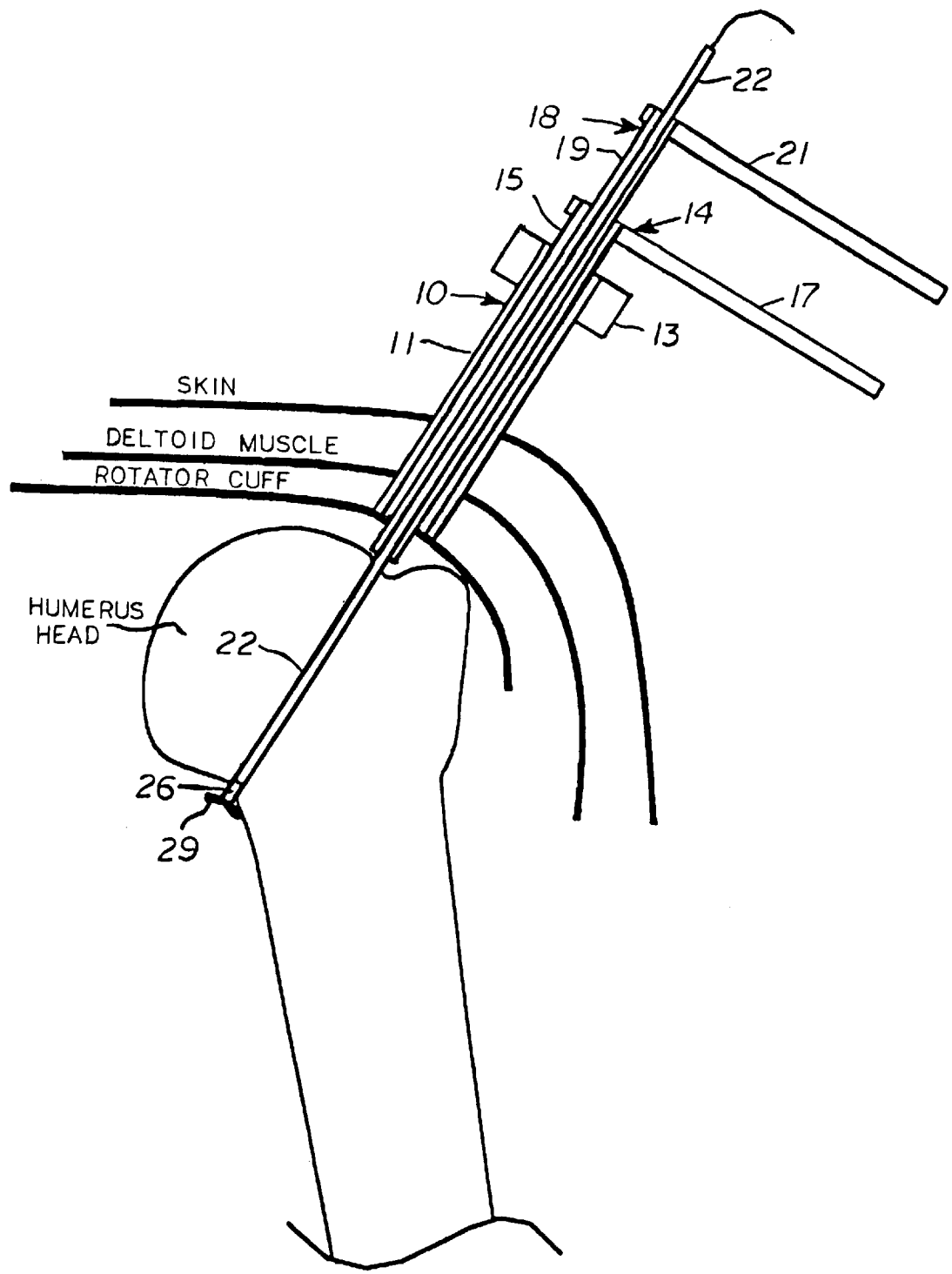

The assembled deployment tool 22 and anchor 26 is pushed downwardly through the inner cannula 18 until the inwardly biased wings 29 of the anchor 26 pass through the drilled hole and exit at the far end, at which point they spring outwardly to resume their original outwardly expanded state (FIG. 6E).

In some cases it may be desirable to place the inner cannula 18 through the drilled hole with its distal end positioned at the far cortex of the humerus head (bottom of the hole). In this situation, the assembled deployment tool 22 and anchor 26 is pushed downwardly until the inwardly biased wings 29 of the anchor 26 clear the distal end of the inner cannula 18, at which point they spring outwardly to resume their original outwardly to resume their original outwardly expanded state (FIG. 6E). The position of the anchor and deployment tool can be determined by reading the graduated markings on the exterior at the proximal end of the deployment tool 22.

After the anchor wings 29 have been deployed, the upper free ends of the sutures are released from the slot 22B of the deployment tool 22, and the deployment tool 22, the inner cannula 18, and the drill guide 14 are removed. The strands of the sutures 30 or 31 which now extend through the drilled hole, the soft tissue of the rotator cuff, and the cannula 10 are pulled upwardly to firmly engage the outspread wings 29 of the anchor 26 against the exterior surface of the far cortex of the humerus head.

Referring again to FIGS. 5A and 5B, the proximal ends of the sutures 30 or 31 are passed through the holes 34 in the button 33, and the button is run down on the suture strands to engage the outer surface of the tendon of the rotator cuff. If the button 33 is provided with the prongs 35, they are pressed into the soft tissue of the cuff.

If the conventional sutures 30 are used, the sutures are tied or knotted in the conventional manner to secure the button 33. If the special sutures 31 having the longitudinally spaced protuberances 32 are used (FIG. 5B), the protuberances will snap through the holes 34 of the button 33 as it is run downwardly on the strands, similar to a cable tie. When the button 33 is properly engaged on the cuff, the excess length of the strands 31 are clipped off, leaving one of the enlarged protuberances 32 engaged on the outer flat surface of the button to secure it in place.

Thus, unlike conventional soft tissues anchors which are anchored in the cancellous bone mass beneath the near cortex of the bone, the present invention provides a suture anchor which is engaged on the exterior of the far cortex of the bone and completely bypasses the cancellous bone mass. The cortex of the bone is much less susceptible to osteopenia than the cancellous interior of the bone.

With the present invention, the sutures are passed through the tissue when the anchor is set, and thus the difficult procedural step and use of devices such as punches and suture relays to pass and tie the sutures through the torn tissue is eliminated.

The calibrated markings on the deployment system of the present invention allows for precise measurement of the far cortex and allows for precise measurement of the depth of insertion and engagement of the anchor device on the far cortex, such that structures beyond the cortex are not violated, and the button hold-down feature of the present invention eliminates the traditionally difficult arthroscopic tying techniques.

The present method of repairing rotator cuff tears is "user friendly" and will allow more surgeons to employ this technique in their daily practice.

While this invention has been described fully and completely with special emphasis upon a preferred embodiment, it should be understood that within the scope of the appended claims the invention may be practiced otherwise than as specifically described herein.

I claim:

1. A system of apparatus for implanting and securing an expandable suture anchor onto a bone for arthroscopic reattachment of torn tissue to the bone, comprising:

a tubular suture anchor deployment tool with proximal and distal ends and an axial bore, said deployment tool distal end configured to releasably receive an expandable suture anchor;

an insertion cannula having a tubular portion with proximal and distal ends, and an axial bore sized to allow passage therethrough of said deployment tool having an expandable suture anchor releasably received on its said distal end and to maintain said anchor in a radially compressed condition during passage therethrough;

an expandable suture anchor having a shank portion with proximal and distal ends;

at least one suture secured at one end to said shank portion proximal end and having a free end extending therefrom;

a plurality of resilient circumferentially spaced wing elements extending radially outward from said shank portion distal end and having free ends spaced from said shank portion, said wing elements capable of being compressed and deflected radially inward when passed through said insertion cannula axial bore and a hole drilled through the bone and resume their outwardly expanded state upon exit therefrom; and a flat circular button member having at least one hole extending through its flat surface through which said at least one suture free end is received, and said button sized to be slidably received through the tubular portion of an outer cannula; wherein said at least one suture free end is placed through said button hole, said button is run down on said at least one suture to engage the outer surface of the torn tissue, and said at least one suture free end is secured over said button such that the torn tissue is secured to the bone by said at least one suture and said at least one suture is anchored to the bone exterior surface by said outwardly expanded wing elements of said suture anchor.

2. The apparatus according to claim 1, further comprising:

longitudinally spaced markings on the exterior of said tubular deployment tool for visually determining the position of said deployment tool distal end during passage through said insertion cannula.

3. The apparatus according to claim 1, further comprising:

a drill guide having a tubular portion with proximal and distal ends and an axial bore sized to allow passage of a drill bit therethrough;

said insertion cannula tubular portion is sized to be received in said drill guide tubular portion axial bore; and longitudinally spaced markings on the exterior of said tubular portion of said insertion cannula for visually determining the position of said insertion cannula distal end during passage through said drill guide tubular portion.

4. The apparatus according to claim 3, further comprising:

an outer cannula having a tubular portion with an axial bore; and said drill guide tubular portion is sized to be received in said outer cannula tubular portion axial bore.

5. The apparatus according to claim 1, further comprising:

an outer cannula having a tubular portion with an axial bore; and said insertion cannula tubular portion is sized to be received in said outer cannula tubular portion axial bore; and longitudinally spaced markings on the exterior of said tubular portion of said insertion cannula for visually determining the position of said insertion cannula distal end during passage through said outer cannula tubular portion.

6. The apparatus according to claim 1, further comprising:

means on said deployment tool for releasably retaining said anchor at said distal end thereof during passage through said insertion cannula axial bore.

7. The apparatus according to claim 1, wherein said at least one suture has a pair of free ends extending from said suture anchor proximal end;

said button member has a pair of holes extending through its flat surface; and said free ends are tied together over said button.

8. The apparatus according to claim 1, wherein said at least one suture has a pair elongate strands extending from said suture anchor proximal end, each said strand having a plurality of longitudinally spaced enlarged diameter protuberances along its length; and said button member has a pair of holes extending through its flat surface of a diameter smaller than said protuberances;

said each of said pair of strands being placed through said button hole and said protuberences snap through said button holes as said button is run down on said pair of strands to engage the outer surface of the torn tissue, and thereafter the excess length of said strands being clipped off to leave one of said enlarged protuberances of each strand engaged on the outer flat surface of said button to secure it on the torn tissue.

9. The apparatus according to claim 1, further comprising:

a plurality of circumferentially spaced prongs depending from one side of said button member configured to be pressed into the torn tissue.

10. Apparatus for anchoring a suture for arthroscopic reattachment of torn tissue to a bone, comprising:

an expandable suture anchor having a shank portion with proximal and distal ends;

at least one suture secured at one end to said shank portion proximal end and having a free end extending therefrom;

a plurality of resilient circumferentially spaced wing elements extending radially outward from said shank portion distal end and having free ends spaced from said shank portion;

said wing elements capable of being compressed and deflected radially inward when passed through a hole smaller in diameter than the wings in their outwardly extended state and resuming their outwardly expanded state upon exit therefrom; and a flat circular button member having at least one hole extending through its flat surface through which said at least one suture free end is received, and said button sized to be slidably received through the axial bore of a tubular cannula; wherein said at least one suture free end is placed through said button hole, said button is run down on said at least one suture to engage the outer surface of the torn tissue, and said at least one suture free end is secured on said button such that the torn tissue is secured to the bone by said at least one suture and said at least one suture is anchored to the bone exterior surface by said outwardly expanded wing elements of said suture anchor.

11. The apparatus according to claim 10, wherein said at least one suture has a pair of free ends extending from said suture anchor proximal end;

said button member has a pair of holes extending through its flat surface; and said free ends are tied together over said button.

12. The apparatus according to claim 10, wherein said at least one suture has a pair elongate strands extending from said suture anchor proximal end, each said strand having a plurality of longitudinally spaced enlarged diameter protuberences along its length; and said button member has a pair of holes extending through its flat surface of a diameter smaller than said protuberances; whereby said each of said pair of strands are placed through said button hole and said protuberances snap through said button holes as said button is run down on said pair of strands to engage the outer surface of the torn tissue, and thereafter the excess length of said strands are clipped off to leave one of said enlarged protuberances of each strand engaged on the outer flat surface of said button to secure it on the torn tissue.

13. The apparatus according to claim 10, further comprising:
a plurality of circumferentially spaced prongs depending from one side of said button member configured to be pressed into the torn tissue.

14. Apparatus for anchoring a suture to a tissue in arthroscopic reattachment of torn tissue, comprising:
at least one elongate suture strand secured at one end to a suture anchor and having a free end extending therefrom and a plurality of longitudinally spaced enlarged diameter protuberances along its length; and
a flat circular button having at least one hole extending through its flat surface of a diameter smaller than said protuberances and through which the free end of said at least one suture strand is passed wherein;
said free end of said at least one suture strand is placed through said button hole and said enlarged protuberances snap through said button hole as said button is run down on said suture strand to engage the outer surface of the torn tissue, and thereafter the excess length of said at least one suture strand is clipped off to leave one of said enlarged protuberances engaged on the outer flat surface of said button such that said button is secured on the torn tissue.

15. The apparatus according to claim 14, further comprising:
a plurality of circumferentially spaced prongs depending from one side of said button member configured to be pressed into the torn tissue.

* * * * *